United States Patent
Dhawan et al.

(10) Patent No.: US 12,018,388 B2
(45) Date of Patent: Jun. 25, 2024

(54) OXYALKYLATED SURFACTANTS AS CORROSION INHIBITORS

(71) Applicant: Ecolab USA Inc., St. Paul, MN (US)

(72) Inventors: Ashish Dhawan, Aurora, IL (US); Jeremy Moloney, Katy, TX (US); Carter M. Silvernail, Burnsville, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 17/337,859

(22) Filed: Jun. 3, 2021

(65) Prior Publication Data

US 2021/0381114 A1   Dec. 9, 2021

Related U.S. Application Data

(60) Provisional application No. 63/178,792, filed on Apr. 23, 2021, provisional application No. 63/034,274, filed on Jun. 3, 2020.

(51) Int. Cl.
*C23F 11/12*      (2006.01)
*C23F 11/173*     (2006.01)

(52) U.S. Cl.
CPC .......... *C23F 11/12* (2013.01); *C23F 11/173* (2013.01)

(58) Field of Classification Search
CPC .... C02F 5/10; C02F 2303/08; C02F 2305/04; C23F 11/04; C23F 11/12; C23F 11/14; C23F 11/141; C23F 11/145; C23F 11/147; C23F 11/149; C23F 11/165; C23F 11/173; C09K 8/54; C09K 2208/32; C10N 2030/12; C10G 1/004; C10G 7/10; C10G 49/005; C10G 75/02
See application file for complete search history.

(56) References Cited

U.S. PATENT DOCUMENTS

| | | | | |
|---|---|---|---|---|
| 3,696,048 A | * | 10/1972 | Hausler | C23F 11/10 252/396 |
| 4,028,117 A | * | 6/1977 | Moat | C23F 11/12 252/396 |
| 4,048,065 A | | 9/1977 | Suen et al. | |
| 4,089,789 A | * | 5/1978 | Muzyczko | C23F 11/04 510/264 |
| 4,212,842 A | * | 7/1980 | Hartke | C23F 11/149 422/12 |
| 4,511,480 A | * | 4/1985 | Outlaw | C23F 11/1673 558/208 |
| 4,636,256 A | * | 1/1987 | Valone | C23F 11/141 564/348 |
| 4,846,980 A | * | 7/1989 | Valone | C23F 11/145 507/260 |
| 4,867,888 A | * | 9/1989 | Valone | C09K 8/54 507/939 |
| 4,975,202 A | * | 12/1990 | Fillipo | C11D 3/042 210/698 |
| 5,082,592 A | * | 1/1992 | McDonald | C23F 11/08 210/698 |
| 5,849,220 A | | 12/1998 | Batton et al. | |
| 6,524,396 B1 | | 2/2003 | Geke et al. | |
| 6,555,012 B1 | | 8/2003 | Fernholz et al. | |
| 6,846,793 B1 | | 1/2005 | Griese | |
| 7,311,144 B2 | | 12/2007 | Conrad | |
| 7,655,158 B2 | * | 2/2010 | Walker | C09K 8/54 252/392 |
| 8,668,779 B2 | | 3/2014 | Cooper et al. | |
| 8,802,605 B2 | | 8/2014 | Rabbat et al. | |
| 10,060,038 B2 | | 8/2018 | Carter et al. | |
| 10,308,886 B2 | | 6/2019 | Rana et al. | |
| 10,550,482 B2 | | 2/2020 | Hatchman et al. | |
| 2012/0232169 A1 | | 9/2012 | Wu et al. | |
| 2017/0198233 A1 | * | 7/2017 | Zhang | C10M 145/38 |
| 2018/0346796 A1 | | 12/2018 | Moloney et al. | |
| 2019/0062187 A1 | | 2/2019 | Dhawan et al. | |

FOREIGN PATENT DOCUMENTS

| | | | |
|---|---|---|---|
| CN | 103058895 A | | 4/2013 |
| GB | 1022878 A | * | 3/1966 |

OTHER PUBLICATIONS

Osman et al., (2002) "Some ethoxylated fatty acids as corrosion inhibitors for low carbon steel in formation water", Materials Chemistry and Physics, 77(1):261-269.

Ahmad et al., (1988) "Corrosion in Fresh Water Systems: Transient Monitoring Technique for Corrosion", Corrosion Engineering, 44(10):750-754.

Ashassi-Sorkhabi et al. (2020) "Influence of fluid flow on the performance of polyethylene glycol as a green corrosion inhibitor", Journal of Adhesion Science and Technology, 34(15):1653-1663.

Ashassi-Sorkhabi et al. (2005) "Inhibition effect of polyethylene glycol on the corrosion of carbon steel in sulphuric acid", Materials Chemistry and Physics, 92:480-486.

Wang et al. (2008) "Study on the interfacial tension of the water solution of a new anionic-non-ionic surfactant and crude oil", XP002804006, retrieved from accession No. 2009:578202 abstract, 2 pages.

\* cited by examiner

*Primary Examiner* — Matthew R Diaz

(74) *Attorney, Agent, or Firm* — Kagan Binder, PLLC

(57) ABSTRACT

Disclosed are oxyalkylated surfactants used in compositions and methods for inhibiting corrosion.

18 Claims, No Drawings

OXYALKYLATED SURFACTANTS AS CORROSION INHIBITORS

CROSS REFERENCE TO RELATED APPLICATIONS

This application claims the benefit of U.S. Provisional Patent Application Ser. Nos. 63/034,274, filed Jun. 3, 2020 and 63/178,792, filed Apr. 23, 2021 the disclosures of which are each incorporated in their entirety herein by reference.

BACKGROUND

Corrosion of metal surfaces continues to be a problem in industrial water systems, including the oil and gas industry. Such systems can include "corrodents" such as salts, other dissolved solids, liquids, gases or combinations thereof that cause, accelerate, or promote corrosion of metal containments that contact the corrodents. These aggressive constituents can cause severe corrosion as evidenced by surface pitting, embrittlement, and general loss of metal. Corrosion problems are even more troublesome in deep-sea operations where replacement of corroded equipment is difficult and costly. As a result, almost all operators in the oil and gas industry employ corrosion inhibitors to reduce corrosion in metal containments, which contact liquids containing corrodents.

A variety of metal corrosion inhibiting formulations that have been developed However, these options are not without their problems. Therefore, there continues to be a need for corrosion inhibiting compositions and methods that are effective and minimize operating costs.

SUMMARY

Described herein are compositions and methods for inhibiting corrosion in fluid sources comprising corrodents.

In one aspect of the application is a method of inhibiting corrosion comprising:
introducing into a fluid source containing corrodents a composition comprising an oxyalkylated surfactant having the general structure as shown in Formula I:

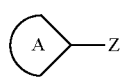

(Formula I)

wherein A is an phenyl, naphthalene, indole, purine, pyridine, quinoline, isoquinoline, pyrimidine, pyrrole, furan, thiophene, imidazole, or thiazole and optionally substituted thereof, and Z has the following structure:

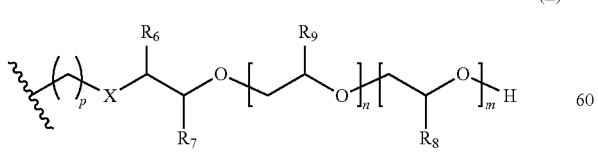

(Z)

wherein X is —O—, —N(R10)—, —OC(O)—, —C(O)O—, —N(R10)C(O)—, —C(O)N(R10)—, —OC(O)O—, —OC(O)N(R10)—, —N(R10)C(O)O—, or —N(R10)C(O) N(R10)—; p is an integer from 0 to 10; R6 is hydrogen, alkyl, or aryl; R7 is alkyl, aryl, or —(CH2)z-O—R11; R8 and R9 are independently hydrogen, alkyl, or aryl; R9 is hydrogen or alkyl; R10 is hydrogen or alkyl; R11 is independently hydrogen or alkyl; m is independently an integer from 2 to 20; n is independently an integer from 3 to 20; and z is an integer from 1 to 10; wherein at least one of R8 and R9 are other than hydrogen, and wherein the composition inhibits corrosion.

In another aspect of the application is a composition comprising a corrosion inhibitor comprising the general structure as shown in Formula I:

(Formula I)

wherein A is an phenyl, naphthalene, indole, purine, pyridine, quinoline, isoquinoline, pyrimidine, pyrrole, furan, thiophene, imidazole, or thiazole and optionally substituted thereof; and Z has the following structure:

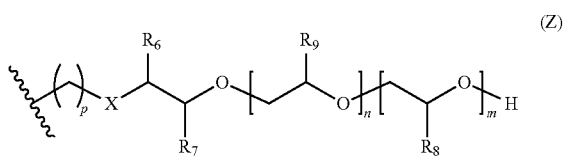

(Z)

wherein X is —O—, —N(R10)—, —OC(O)—, —C(O)O—, —N(R10)C(O)—, —C(O)N(R10)—, —OC(O)O—, —OC(O)N(R10)—, —N(R10)C(O)O—, or —N(R10)C(O) N(R10)—; p is an integer from 0 to 10; R6 is hydrogen, alkyl, or aryl; R7 is alkyl, aryl, or —(CH2)z-O—R11; R8 and R9 are independently hydrogen, alkyl, or aryl; R9 is hydrogen or alkyl; R10 is hydrogen or alkyl; R11 is independently hydrogen or alkyl; m is independently an integer from 2 to 20; n is independently an integer from 3 to 20; and z is an integer from 1 to 10; wherein at least one of R8 and R9 are other than hydrogen, and wherein the composition inhibits corrosion.

In some aspects, the compound of Formula 1 corresponds to a structure of Formula II:

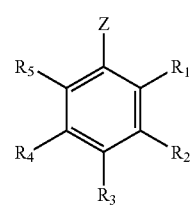

wherein R1, R2, R3, R4, and R5 are independently hydrogen, Z, alkyl, alkoxyl, or two adjacent R groups combine to form a fused ring.

In still other aspects, the compound of Formula 1 corresponds to a structure of Formula III:

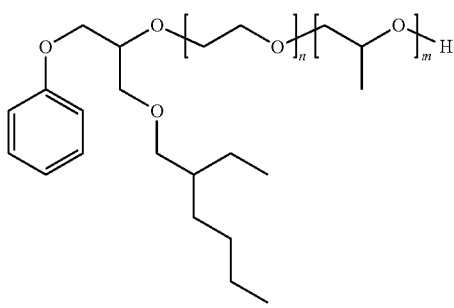

wherein n is an integer from 10 to 20 and m is an integer from 2 to 12.

DETAILED DESCRIPTION

Although the present disclosure provides references to various embodiments, persons skilled in the art will recognize that changes may be made in form and detail without departing from the spirit and scope of the application. Reference to various embodiments does not limit the scope of the claims attached hereto. Additionally, any examples set forth in this specification are not intended to be limiting and merely set forth some of the many possible embodiments for the appended claims.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present application. All publications, patent applications, patents and other references mentioned herein are incorporated by reference in their entirety.

As used herein, the term "aliphatic" or "aliphatic group" refers to a straight-chain or branched hydrocarbon chain that is completely saturated or that contains one or more units of unsaturation, or a monocyclic hydrocarbon or bicyclic hydrocarbon that is completely saturated or that contains one or more units of unsaturation, but which is not aromatic.

As used herein, the term "alkyl group" as described herein alone or as part of another group is an optionally substituted linear saturated monovalent hydrocarbon substituent containing from one to sixty carbon atoms or one to thirty carbon atoms in the main chain or eight to thirty carbon atoms in the main chain, or an optionally substituted branched saturated monovalent hydrocarbon substituent containing three to sixty carbon atoms, or eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "alkoxy" as used herein or alone or as part of another group is an —OR group, wherein the R group is a substituted or unsubstituted alkyl group as defined herein.

The terms "aryl" or "ar" as used herein alone or as part of another group (e.g., aralkyl) denote optionally substituted homocyclic aromatic groups, or monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

As used herein, the term "corrodents," are materials that cause, initiate, catalyze, accelerate, induce, or otherwise promote the corrosion of metals.

As used herein, the term "corrosion inhibitor" means a compound or mixture that prevents, retards, mitigates, reduces, controls and/or delays corrosion.

As used herein, the term "inhibits," "inhibiting," or grammatical equivalents thereof when used in the context of corrosion inhibition refers to preventing, retarding, mitigating, reducing, controlling and/or delaying corrosion.

As used herein, the term "injectate" means water plus any solids or liquids dispersed therein that is injected into a subterranean formation for the purpose of inducing hydrocarbon recovery therefrom. Injectates optionally include salts, polymers, surfactants, scale inhibitors, stabilizers, metal chelating agents, corrosion inhibitors, paraffin inhibitors, and other additives as determined by the operator in a subterranean hydrocarbon recovery process.

As used herein, the term "passivation" means the prevention of a reaction between two materials when used together by coating at least one of the two materials to such an extent that they become substantially less reactive relative to each other As used herein, the term "produced water" means water that flows back from a subterranean reservoir and is collected during a hydrocarbon recovery process including, but not limited to hydraulic fracturing and tertiary oil recovery. Produced water includes residual hydrocarbon products entrained therein and one or more of injectate, connate (native water present in the subterranean formation along with the hydrocarbon), brackish water, and sea water. Produced water ranges in temperature from about −30° C. to about 200° C., depending on the subterranean reservoir and the terranean environment and infrastructure proximal to the subterranean reservoir.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may, but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the term "substantially" means "consisting essentially of" and includes "consisting of," and these terms are construed as in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

The term "substituted" as in "substituted aryl, "substituted alkyl," and the like, means that in the group in question (e.g., the alkyl, aryl or other group that follows the term), at least one hydrogen atom bound to a carbon atom is replaced with one or more substituent groups such as hydroxy (—OH), alkylthio, phosphino, amido (CON(RA)(RB), wherein RA and RB are independently hydrogen, alkyl, or aryl), amino (N(RA)(RB), wherein RA and RB are independently hydrogen, alkyl, or aryl), halo (fluoro, chloro, bromo, or iodo), silyl, nitro (—NO2), an ether (—ORA wherein RA is alkyl or aryl), an ester (—OC(O)RA wherein RA is alkyl or aryl), keto (—C(O)RA wherein RA is alkyl or aryl), heterocyclo, and the like. When the term "substituted" introduces a list of possible substituted groups, it is intended that the term apply to every member of that group. That is, the phrase "optionally" substituted alkyl or aryl" is to be interpreted as optionally substituted alkyl or optionally substituted aryl.

As used herein, any recited ranges of values contemplate all values within the range and are to be construed as support for claims reciting any sub-ranges having endpoints which are real number values within the recited range. By way of example, a disclosure in this specification of a range from 1 to 5 shall be considered to support claims to any of the following ranges: 1-5; 1-4; 1-3; 1-2; 2-5; 2-4; 2-3; 3-5; 3-4; 4-5 and any values there between.

Described herein are compositions and methods directed to oxyalkylated surfactants. In some embodiments, the oxyalkylated surfactants are used to inhibit corrosion of metal containments that contact fluids containing corrodents. The compositions may be applied to one or more fluids to inhibit or reduce corrosion in water systems such as a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system transport, or any storage, and refining equipment such as pipes, transfer lines, valves, and the like.

Below is the general formula or Formula (I) of the oxyalkylated surfactants:

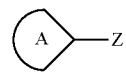

(Formula I)

wherein A is an phenyl, naphthalene, indole, purine, pyridine, quinoline, isoquinoline, pyrimidine, pyrrole, furan, thiophene, imidazole, or thiazole and optionally substituted thereof, and Z has the following structure:

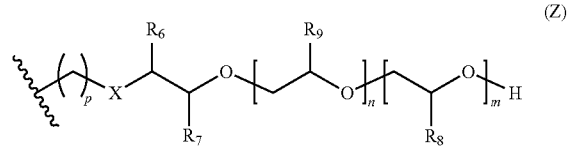

(Z)

wherein X is —O—, —N(R10)—, —OC(O)—, —C(O)O—, —N(R10)C(O)—, —C(O)N(R10)—, —OC(O)O—, —OC(O)N(R10)—, —N(R10)C(O)O—, or —N(R10)C(O)N(R10)—; p is an integer from 0 to 10; R6 is hydrogen, alkyl, or aryl; R7 is alkyl, aryl, or —(CH2)z-O—R11; R8 and R9 are independently hydrogen, alkyl or aryl; R10 is hydrogen or alkyl; R11 is hydrogen or alkyl; m is independently an integer from 2 to 20; n is independently an integer from 3 to 20; and z is an integer from 1 to 10, wherein at least one of R8 and R9 are other than hydrogen.

In some embodiments, the oxyalkylated surfactant has the structure of Formula II:

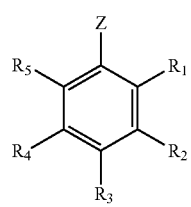

(Formula II)

wherein R1, R2, R3, R4, and R5 are independently hydrogen, Z, alkyl, alkoxy, or two adjacent R groups combine to form a fused ring.

In some embodiments, the oxyalkylated surfactant has R1, R2, R3, R4, and R5 independently be hydrogen or C1 to C4 alkyl.

The oxyalkylated surfactants of Formula 2 described herein can have R6 be hydrogen. In some embodiments the oxyalkylated surfactants of Formula 2 can have R8 be methyl or benzyl. In some embodiments, the oxyalkylated surfactants of Formula 2 can have R9 be hydrogen. The oxyalkylated surfactants of Formula 2 can further have R7 be —(CH2)z-O—R11. In some embodiments, when R7 is —(CH2)z-O—R11, z is 1 to 3. In other embodiments, when R7 is —(CH2)z-O—R11, z is 1. In some embodiments the oxyalkylated surfactants of Formula 2 described herein can have R11 be C4 to C22 alkyl. In some embodiments, the oxyalkylated surfactants of Formula 2 can have X be —O— or —N(R10)—. In some embodiments, the oxyalkylated surfactants of Formula 2 can have X be —O—. In other embodiments, the oxyalkylated surfactants of Formula 2 can have X be —N(R10)—. The compound of Formula 2 can have R10 be hydrogen.

In some embodiments, the oxyalkylated surfactant has the structure corresponding to Formula III

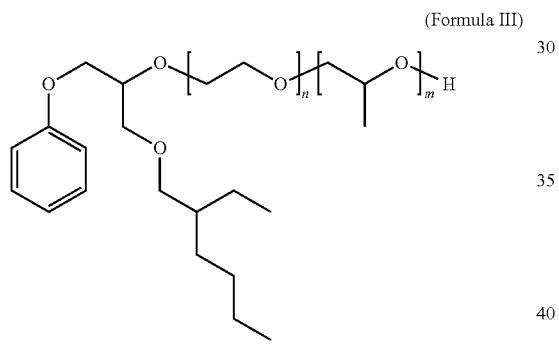

(Formula III)

wherein n is an integer from 10 to 20 and m is an integer from 2 to 12; or, wherein n is an integer of 16 or 18 and m is an integer from 4 to 8.

The overall synthesis of the oxyalkylated surfactants described herein is achieved in two steps (Scheme 1). Acceptor molecule (C) is first prepared by ring opening reaction of an alkyl-epoxide (B) with an aromatic amine or alcohol compound (A). The second step involves oxyalkylation of the acceptor molecule (C) with one or more alkylene oxides (D & E) to afford a series of surfactants (F).

Scheme 1

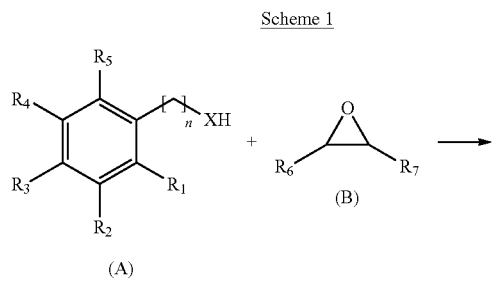

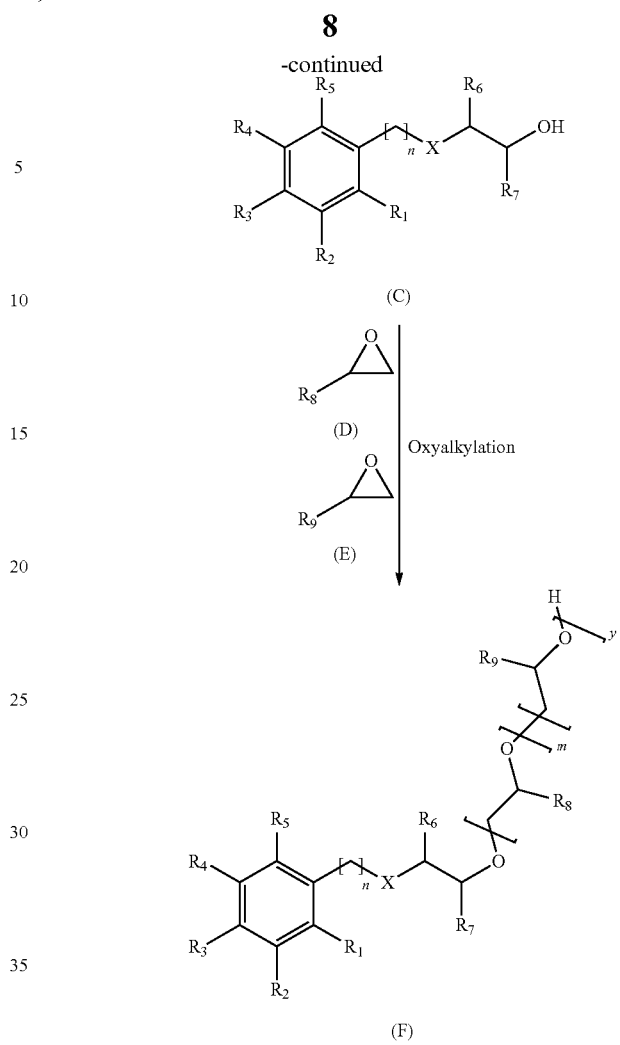

wherein X is —O—, —N(R10)—, —OC(O)—, —C(O)O—, —N(R10)C(O)—, —C(O)N(R10)—, —OC(O)O—, —OC(O)N(R10)—, —N(R10)C(O)O—, or —N(R10)C(O)N(R10)—; n is an integer from 0 to 10; R6 and R9 are independently hydrogen, alkyl, or aryl; R7 is alkyl, aryl, or —(CH2)z-O—R1, R8 is independently hydrogen, alkyl, or aryl; R10 is hydrogen, alkyl, or Z; R11 is hydrogen or alkyl; m is independently an integer from 3 to 20; y is independently an integer from 3 to 20; and z is an integer from 1 to 10; and R1, R2, R3, R4, and R5 are independently hydrogen, Z, alkyl, alkoxyl, or two adjacent R groups combine to form a fused ring. In some embodiments, R8 is hydrogen and R9 is methyl.

In some embodiments, Formula III is as described in Example 1, wherein n is an integer from 10 to 20 and m is an integer from 2 to 12; or n is an integer of 16 or 18 and m is an integer from 4 to 8.

The compositions and methods described herein are used to inhibit corrosion. In some embodiments, compositions comprise, consist essentially of, or consist of the described oxyalkylated surfactants used for corrosion inhibition. In some embodiments, Formula III is as described in Example 1, wherein n is an integer from 10 to 20 and m is an integer from 2 to 12; or n is an integer of 16 or 18 and m is an integer from 4 to 8 and such compounds are used for corrosion inhibition.

In some embodiments, the oxyalkylated surfactants or compositions containing them include other additives such as one or more asphaltene inhibitors, paraffin inhibitors, scale inhibitors, demulsifiers, water clarifiers, dispersants, emulsion breakers, antifoams, biocides, acids, carriers or any combination thereof. In some embodiments, examples of other additives used in the present compositions are disclosed in U.S. patent application Ser. No. 16/116,413 filed Aug. 29, 2018 (US Pat. App. Pub. No. 2019/0062187A1) and incorporated herein by reference in its entirety.

In some embodiments, the oxyalkylated surfactants further comprises one or more solvents or a mixture thereof. In some embodiments, a composition which includes solvents suitable for formulation of the oxyalkylated surfactants are water, brine, seawater, alcohols such as methanol, ethanol, isopropanol, n-propanol, n-butanol, isobutanol, sec-butanol, t-butanol or higher alcohols such as benzyl alcohol); ketones such as acetone, or methyl ethyl ketone (2-butanone); acetonitrile; esters such as ethyl acetate, propyl acetate and butyl acetate; ethers such as diethyl ether or higher, e.g. methyl t-butyl ether, glyme, diglyme, ethylene glycol monobutyl ether, ethylene diglycol ethyl ether, 1,4 dioxane and related; aromatics such as toluene, xylene(s), diethylbenzene, naphthalene and related aromatics or refinery cuts (heavy aromatic naptha, heavy aromatic distillates, and related); aliphatics such as pentane, hexane, heptane, octane, or refined gasoline; or several "green" solvents such as 2-methyltetrahydrofuran, furfural alcohol, and cyclopentylmethylether.

In some embodiments, the solvents suitable for formulation with the oxyalkylated surfactants are aliphatic, such as pentane, hexane, cyclohexane, methylcyclohexane, heptane, decane, dodecane, diesel, and the like, and aromatics, such as toluene, xylene, heavy aromatic naphtha, fatty acid derivatives (acids, esters, amides), and the like.

In some embodiments, the composition can include solvents disclosed in U.S. patent application Ser. No. 15/992,383 filed May 30, 2018 (US Pat. App. Pub. No. 20180346796A1) and US Pat. App. Pub. No. 2019/0062187A1, each document incorporated herein by reference in its entirety.

In some embodiments, the solvents used to enhance the corrosion performance of the compositions containing the oxyalkylated surfactants are sulfur containing compounds. In some embodiments the other sulfur-containing compounds are, thioglycolic acid, 3,3'-dithiodipropionic acid, thiosulfate, thiourea, 2-mercaptoethanol, L-cysteine, and tert-butyl mercaptan.

In some embodiments the one or more solvents are 10 wt % to 99 wt % of the composition; 1-25 wt %, 20-50 wt %, 30-75 wt %, 50-75%, 75-99 wt % of the composition.

In some embodiments, the oxyalkylated surfactants are provided neat (viz., without a solvent). In some embodiments, the oxyalkylated surfactants further include dissolving or dispersing the oxyalkylated surfactants in water or water mixed with a water-soluble solvent before applying the oxyalkylated surfactants. In some embodiments, the oxyalkylated surfactants are provided as a concentrate. In some embodiments the method includes applying an oxyalkylated surfactant concentrate directly to a metal containment in an amount that results in 0.1 ppm to 10,000 ppm ppm (by weight or by volume) of the oxyalkylated surfactants in the fluid source. In other embodiments the method further includes diluting oxyalkylated surfactants concentrate prior to the introducing. The diluting comprises, consists essentially of, or consists of combining oxyalkylated surfactant concentrate with a diluent, wherein the diluent comprises, consists essentially of, or consists of water, a water source, a water soluble solvent, or a mixture of two or more thereof; and optionally includes mixing the oxyalkylated surfactants concentrate with the diluent prior to the introducing of the oxyalkylated surfactants to the fluid source.

In some embodiments, the oxyalkylated surfactants or in a composition is used in a method of inhibiting corrosion in a fluid source. The fluid source can be contained in a metal container or in contact with pipelines used to transport fluid sources toward, into, out of a subterranean formation. In some embodiments, the fluid source contains corrodents. In some embodiments, the corrodents include hydrogen sulfide, carbon dioxide, oxygen, sodium chloride, calcium chloride, sulfur dioxide, or combination thereof. In some embodiments, the fluid source comprises water, gas, and optionally liquid hydrocarbon or combinations thereof. In some embodiments, the fluid source is produced water or an injectate. In some embodiments, the metal containment is a tank, pipe, or other apparatus having a metal surface in contact with a fluid source, or potentially in contact with a fluid source, wherein the fluid source includes one or more corrodents.

In some embodiments, the oxyalkylated surfactants inhibit corrosion of the metal surface more effectively than a conventional imidazoline corrosion inhibitors (e.g. TOFA: DETA imidazoline) or quaternary corrosion inhibitors (e.g. dimethyl benzyl ammonium chloride).

In some embodiments, the pH of the fluid source is less than 7. In some embodiments, the pH of the fluid source is between about 1 and about 6, between 5 and 6, between 4 and 5, between 3 and 4, between 2 and 3, between 1 and 2, or between 0 and 1.

In some embodiments, various dosage amounts of the composition and/or the oxyalkylated surfactants are introduced to a fluid source to inhibit corrosion of a metal containment in contact with the fluid source. One of ordinary skill in the art is able to calculate the amount of oxyalkylated surfactants or composition comprising oxyalkylated surfactants for a given situation without undue experimentation. Factors that would be considered important in such calculations include, for example, content of fluid source, content of corrodents, percentage water cut, and similar parameters.

In some embodiments, the composition comprising the oxyalkylated surfactants is applied to a fluid source that contains various levels of water cut. One of ordinary skill in the art understands that "water cut" refers to the water percentage in a hydrocarbon phase (e.g. oil) and water mixture. In one embodiment, the water cut is from about 1% to about 80% w/w with respect to the hydrocarbon phase. In other embodiments, the water cut is from about 1% to about 30% w/w, from about 5% to about 40% w/w, from about 10% to about 60% w/w, from about 15% to about 80% w/w with respect to the hydrocarbon phase.

In some embodiments, the oxyalkylated surfactants or in a composition is applied to a fluid source that contains various levels of salinity. In some embodiments, the fluid source has a salinity of about 0.1% to about 25% or about 10% to about 25% weight/weight (w/w) total dissolved solids.

In other embodiments the oxyalkylated surfactants or in a composition is applied to a fluid source that contains fresh water, recycled water, salt water, surface water, produced water, a liquid hydrocarbon or a mixture thereof.

In some embodiments, the methods of inhibiting corrosion are in a water system. In some embodiments the water system is a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system. Other systems that the oxyalkylated surfactants or in a composition can be applied to are disclosed in U.S. patent application Ser. No. 16/116,413 filed Aug. 29, 2018 (US Pat. App. Pub. No. 2019/0062187A1) and incorporated herein by reference in its entirety.

In some embodiments, the oxyalkylated surfactants or in a composition are used in an amount from about 0.1 ppm to 10,000 ppm; from about 100 ppm to 1000 ppm; from about 500 ppm to 3000 ppm; from about 750 ppm to 3,000 ppm; from about 5000 ppm to 2,000 ppm; from about 5000 ppm to 3,000 ppm; from about 100 ppm to 3,000 ppm; from about 1 ppm to 100 ppm, from about 10 ppm to 50 ppm; from about 50 ppm to 100 ppm, from about 1 ppm to 50 ppm; from about 1 ppm to 20 ppm; from about 1 ppm to 5 ppm; from about 3 ppm to 20 ppm; from 0.1 ppm to 5 ppm; or from about 0.1 ppm to 1 ppm by weight or volume of the oxyalkylated surfactants in the fluid source.

In some embodiments, the oxyalkylated surfactants provides from about 50-99%, 75-99%, or 75-50% corrosion inhibition for containment in contact with a fluid source. In some embodiments, the oxyalkylated surfactants provides from about 50-99% corrosion protection for a containment in contact with a fluid source, as determined by a 1018 carbon steel coupon in a bubble test as described in Example 4. In some embodiments, the method provides at least 70% corrosion protection for a 1018 carbon steel coupon in a bubble test, from about 70-90%, 75-85% or 80-90% wherein the bubble test is characterized by a testing temperature of about 80° C.; a $CO_2$ saturated liquid medium of 100% brine; a test duration of 2-3 hours; and an corrosion inhibitor dosage of 10 ppm, 20 ppm, 50 ppm, 75 ppm, 100 ppm, 200 ppm, 300 ppm, 400 ppm, 500 ppm, 1,000 ppm, 5,000, 7,500 ppm, or 15,000 ppm based on total fluids.

In some embodiments, the method provides at least 65% protection, from about 65-80%, 70-90%, 75-85% or 80-90% after two hours, at least 85% protection after 8 hours, and about 100% protection 10 hours.

In some embodiments, the oxyalkylated surfactants are more effective, on a weight basis, at inhibiting corrosion than at least known quaternary or imidazoline chemistries.

In some embodiments the oxyalkylated surfactants is introduced into a fluid source by any means suitable for ensuring dispersal of the oxyalkylated surfactants through the fluid source being treated. The composition comprising the oxyalkylated surfactants can be injected as prepared or formulated in one or more additional solvents, depending upon the application and requirements. One of skill in the art will understand that the methods disclosed herein are not limited in any way by the introduction method, the timing or the location of the introduction.

In some embodiments, the oxyalkylated surfactants are introduced to a fluid using various well-known methods and they may be introduced at numerous, different locations throughout a given system. In one embodiment, the composition comprising the oxyalkylated surfactant chemistry is pumped into an oil/gas pipeline using an umbilical line. In some embodiments, capillary string injection systems may be utilized to deliver the composition. U.S. Pat. No. 7,311,144 provides a description of an apparatus and methods relating to capillary injection, the disclosure of which is incorporated into the present application in its entirety. In other embodiments, the composition comprising the one or more oxyalkylated surfactants are injected using mechanical equipment such as chemical injection pumps, piping tees, injection fittings, and the like.

Introducing may be achieved also by mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition into the fluid source. The contacting can be made in-line and/or offline. The various components of the composition may be mixed prior to and/or during contact.

The application is further described below with additional non-limiting embodiments:

1. A method of inhibiting corrosion comprising:
   introducing into a fluid source containing corrodents a composition comprising an oxyalkylated surfactant having the general structure as shown in Formula I:

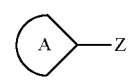

(Formula I)

wherein A is an phenyl, naphthalene, indole, purine, pyridine, quinoline, isoquinoline, pyrimidine, pyrrole, furan, thiophene, imidazole, or thiazole and optionally substituted thereof, and Z has the following structure:

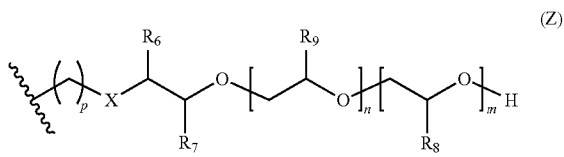

(Z)

wherein X is —O—, —N(R10)—, —OC(O)—, —C(O)O—, —N(R10)C(O)—, —C(O)N(R10)—, —OC(O)O—, —OC(O)N(R10)—, —N(R10)C(O)O—, or —N(R10)C(O) N(R10)—; p is an integer from 0 to 10; R6 is hydrogen, alkyl, or aryl; R7 is alkyl, aryl, or —(CH2)z-O—R11; R8 and R9 are independently hydrogen, alkyl, or aryl; R9 is hydrogen or alkyl; R10 is hydrogen or alkyl; R11 is independently hydrogen or alkyl; m is independently an integer from 2 to 20; n is independently an integer from 3 to 20; and z is an integer from 1 to 10; wherein at least one of R8 and R9 are other than hydrogen, and wherein the composition inhibits corrosion.

2. The method of embodiment 1, wherein introducing comprises by injecting or pumping.

3. The method as in one of embodiments 1-2, wherein the fluid source contacts a metal containment.

4. The method as in one of embodiments 1-3, wherein the fluid source is contained in an oil or gas pipeline, refinery, distillation columns, stripper trays or piping.

5. The method as in one of embodiments 1-4, wherein the fluid source comprises fresh water, recycled water, salt water, surface water, produced water, a liquid hydrocarbon or a mixture thereof.

6. The method as in one of embodiments 1-5, wherein the fluid source comprises about 0.1% to about 25% weight/weight total dissolved solids.

7. The method as in one of embodiments 1-6, wherein A is an phenyl, naphthyl, pyridyl, quinolyl, isoquinolyl or optionally substituted equivalent thereof.

8. The method as in one of embodiments 1-7, wherein A is phenyl or naphthyl or optionally substituted equivalent thereof.

9. The method of any one of embodiments 1 to 8, wherein the compound of Formula 1 corresponds to a structure of Formula II:

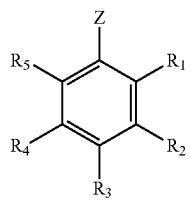

wherein R1, R2, R3, R4, and R5 are independently hydrogen, Z, alkyl, alkoxyl, or two adjacent R groups combine to form a fused ring.

10. The method as in one of embodiments 1-9, wherein R1, R2, R3, R4, and R5 are independently hydrogen or C1 to C4 alkyl.

11. The method as in one of embodiments 1-10, wherein R1, R2, R3, R4, and R5 are hydrogen.

12. The method as in one of embodiments 1-11, wherein R6 is hydrogen.

13. The method as in one of embodiments 1-12, wherein R8 is methyl or benzyl.

14. The method as in one of embodiments 1-13, wherein R9 is hydrogen.

15. The method of any one of embodiments 1 to 14, wherein R7 is —(CH2)z-O—R11.

16. The method as in one of embodiments 1-15, wherein z is 1 to 3.

17. The method as in one of embodiments 1-16, wherein z is 1.

18. The method as in one of embodiments 1-17, wherein R11 is C4 to C22 alkyl.

19. The method as in one of embodiments 1-18, wherein X is —O— or —N(R10)—.

20. The method as in one of embodiments 1-19, wherein X is —O—.

21. The method as in one of embodiments 1-20, wherein X is —N(R10)—.

22. The method as in one of embodiments 1-21, wherein R10 is hydrogen.

23. The method as in one of embodiments 1-22, wherein the compound of Formula 1 or 2 has a structure corresponding to Formula III.

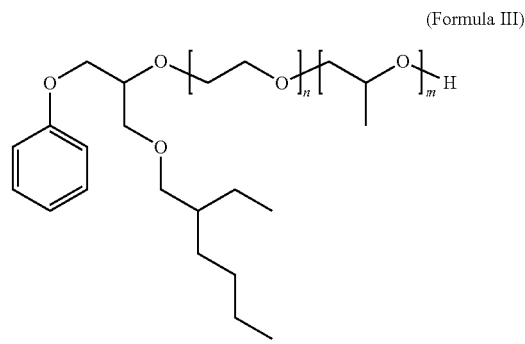

wherein n is an integer from 10 to 20 and m is an integer from 2 to 12.

24. The method of embodiment 23, wherein n is an integer of 16 or 18 and m is an integer from 4 to 8.

25. The method as in one of embodiments 1-24, wherein the oxyalkylated surfactant is added to the fluid source from 1 ppm to 3,000 ppm.

26. The method as in one of embodiments 1-25, wherein the composition further comprises an asphaltene inhibitors, paraffin inhibitors, scale inhibitors, demulsifiers, water clarifiers, dispersants, emulsion breakers, antifoams, a salt, or a mixture thereof.

27. The method as in one of embodiments 1-26, wherein the oxyalkylated surfactant provides at least 70% corrosion protection in a 1018 carbon steel coupon test.

28. A composition comprising a corrosion inhibitor comprising the general structure as shown in Formula I:

wherein A is an phenyl, naphthalene, indole, purine, pyridine, quinoline, isoquinoline, pyrimidine, pyrrole, furan, thiophene, imidazole, or thiazole and optionally substituted thereof, and Z has the following structure:

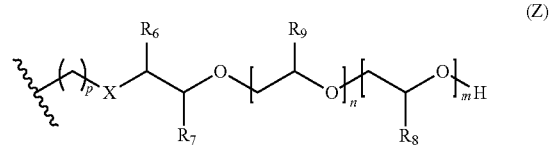

wherein X is —O—, —N(R10)—, —OC(O)—, —C(O)O—, —N(R10)C(O)—, —C(O)N(R10)—, —OC(O)O—, —OC(O)N(R10)—, —N(R10)C(O)O—, or —N(R10)C(O)N(R10)—; p is an integer from 0 to 10; R6 is hydrogen, alkyl, or aryl; R7 is alkyl, aryl, or —(CH2)z-O—R11; R8 and R9 are independently hydrogen, alkyl, or aryl; R9 is hydrogen or alkyl; R10 is hydrogen or alkyl; R11 is independently hydrogen or alkyl; m is independently an integer from 2 to 20; n is independently an integer from 3 to 20; and z is an integer from 1 to 10; wherein at least one of R8 and R9 are other than hydrogen, and wherein the composition inhibits corrosion.

29. The composition of embodiment 28, wherein A is an phenyl, naphthyl, pyridyl, quinolyl, isoquinolyl, or optionally substituted equivalent thereof.

30. The composition as in one of embodiments 28-29, wherein A is phenyl, naphthyl, or optionally substituted equivalent thereof.

31. The composition as in one of embodiments 28-30, wherein the compound of Formula 1 corresponds to a structure of Formula II:

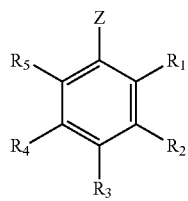

wherein R1, R2, R3, R4, and R5 are independently hydrogen, Z, alkyl, alkoxyl, or two adjacent R groups combine to form a fused ring.

32. The composition as in one of embodiments 28-31, wherein R1, R2, R3, R4, and R5 are independently hydrogen or C1 to C4 alkyl.

33. The composition as in one of embodiments 28-32, wherein R1, R2, R3, R4, and R5 are hydrogen.

34. The composition as in one of embodiments 28-33, wherein R6 is hydrogen.

35. The composition as in one of embodiments 28-34, wherein R8 is methyl or benzyl.

36. The composition as in one of embodiments 28-35, wherein R9 is hydrogen.

37. The composition as in one of embodiments 28-36, wherein R7 is —(CH2)z-O—R11.

38. The g composition as in one of embodiments 28-37, wherein z is 1 to 3.

39. The composition as in one of embodiments 28-38, wherein z is 1.

40. The composition as in one of embodiments 28-39, wherein R11 is C4 to C22 alkyl.

41. The composition as in one of embodiments 28-40, wherein X is —O— or —N(R10)—.

42. The composition as in one of embodiments 28-41, wherein X is —O—.

43. The composition as in one of embodiments 28-42, wherein X is —N(R10)—.

44. The composition as in one of embodiments 28-43, wherein R10 is hydrogen.

45. The composition as in one of embodiments 28-44, wherein the compound of Formula 1 or 2 has a structure corresponding to Formula III:

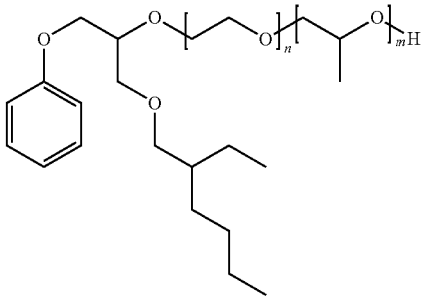
(Formula III)

wherein n is an integer from 10 to 20 and m is an integer from 2 to 12.

46. The composition as in one of embodiments 28-45, wherein n is an integer of 16 or 18 and m is an integer from 4 to 8.

47. The a composition as in one of embodiments 28-46, wherein the composition further comprises an asphaltene inhibitors, paraffin inhibitors, scale inhibitors, demulsifiers, water clarifiers, dispersants, emulsion breakers, antifoams, a salt, or a mixture thereof.

48. A treated metal containment comprising:

a metal containment comprising a metal surface; and the fluid source comprising the oxyalkylated surfactants as in one of embodiments 28-47, wherein at least a portion of the metal surface is contacted by the fluid source.

49. The treated metal containment as in one of embodiments 28-48, wherein the metal containment comprises a tank or pipe.

50. Use of the oxyalkylated surfactants as in one of embodiments 1-49 to inhibit corrosion.

51. Use of the oxyalkylated surfactants as in one of embodiments 1-49 to treat a fluid source comprising one or more corrodents.

52. Use of the oxyalkylated surfactants as in one of embodiments 1-49 to inhibit corrosion of a metal containment comprising a fluid source comprising one or more corrodents.

Examples

The following examples are intended to illustrate different aspects and embodiments of the specification and are not to be considered limiting the scope of the specification. It will be recognized that various modifications and changes may be made to the experimental embodiments described herein and without departing from the scope of the claims.

Example 1: Synthesis of acceptor molecule 1-((2-ethylhexyl)oxy)-3-phenoxypropan-2-ol 1-((2-ethylhexyl)oxy)-3-phenoxypropan-2-ol is first prepared as an acceptor molecule by base-catalyzed ring opening reaction of 2-ethylhexylglycidal ether with phenol. The second step involves oxyalkylation of the acceptor molecule (1 mole) with ethylene oxide first (7-13 moles) and then propylene oxide to afford a series of surfactants (Table 2). The synthesis reaction scheme for preparation of surfactant compositions is shown in Scheme 1.

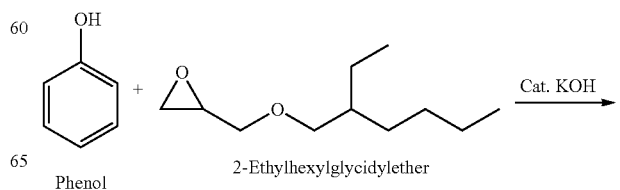
Phenol + 2-Ethylhexylglycidylether →(Cat. KOH)

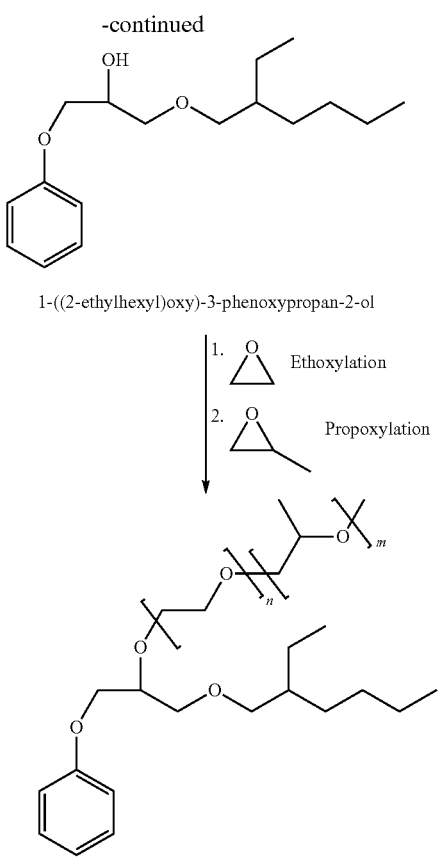

1-((2-ethylhexyl)oxy)-3-phenoxypropan-2-ol

Synthesis of
1-((2-ethylhexyl)oxy)-3-phenoxypropan-2-ol

Phenol (100 g, 1.06 mole) and potassium hydroxide (1 g, 0.02 mole) were added to a 500 mL three necked round-bottom flask equipped with temperature probe, condenser, nitrogen inlet and magnetic stir bar and the temperature of the reaction increased to 50° C. 2-Ethylhexylglycidal ether (200 g, 1.06 moles) was then added to the molten phenol under nitrogen blanket. The temperature of the reaction was further increased to 130° C. and stirred for 4 hours or until completion of reaction. Reagents used in the reaction are summarized in Table 1.

TABLE 1

Reagents for synthesis of 1-((2-ethylhexyl)oxy)-3-phenoxypropan-2-ol.

| Reagent | MW(g/mol) | Mass(g) | n(mole) |
|---|---|---|---|
| Phenol | 94.11 | 100 | 1.06 |
| Ethylhexyl glycidyl ether | 186.29 | 200 | 1.06 |
| KOH Pellets | 56.11 | 1 | 0.02 |

Example 2: Addition of ethylene oxide to the
1-((2-ethylhexyl)oxy)-3-phenoxypropan-2ol After catalyzing and dehydrating, 2967.2 g of 1-((2-ethylhexyl)oxy-3phenoxypropan-2-ol was charged to a oxyalkylation reactor and heated to 125° C. under 10 psi of nitrogen at a stirrer speed of 300 rpm. The ethoxylation reaction was initiated when the acceptor material reached 125° C. The ethylene oxide was charged in step-wise fashion to slowly increase the working pressure range of 55-65 psi during the oxide feed. A slight exotherm was observed. Once the target amount of ethylene oxide, 7477 g (16 mol), was charged to the reactor, the oxide feed was discontinued and the reaction was allowed to proceed for 6 hours at 125° C. The material was then cooled and sampled for testing. Preparation of intermediate with 18 mole of ethylene oxide) was completed through addition of the desired amounts of EO.

Example 3: Addition of propylene oxide to the ethoxylated
1-((2-ethylhexyl)oxy)-3phenoxypropan-2-ol After catalyzing and dehydrating, ethoxylated 1-((2-ethylhexyl)oxy-3phenoxypropan-2-ol was charged to a Parr reactor and heated to 125° C. under 10 psi of nitrogen at a stirrer speed of 300 rpm. The propoxylation reaction was initiated when the acceptor material reached 125° C. The propylene oxide was charged in step-wise fashion to slowly increase the working pressure range of 55-65 psi during the oxide feed. A slight exotherm was observed. Once the target amount of propylene oxide was charged to the reactor, the oxide feed was discontinued and the reaction was allowed to proceed for 6 hours at 125° C. The material was then cooled and sampled for testing. Preparation of intermediates with increasing levels of propylene oxide (4-8 mol PO) was completed through addition of the desired amounts of propylene oxide. The samples synthesized for corrosion evaluation are shown in Table 2.

TABLE 2

Samples synthesized and evaluated for corrosion testing

| Sample ID | n | m |
|---|---|---|
| CI-1 | 16 | 4 |
| CI-2 | 16 | 5 |
| CI-3 | 16 | 6 |
| CI-4 | 16 | 7 |
| CI-5 | 16 | 8 |
| CI-6 | 18 | 4 |
| CI-7 | 18 | 5 |
| CI-8 | 18 | 6 |
| CI-9 | 18 | 7 |
| CI-10 | 18 | 8 |

Example 4: Corrosion Testing

The bubble cell test was used to investigate the effectiveness of the oxyalkylated surfactant chemistries as corrosion inhibitors. This test measures the corrosion rate of a steel electrode by aqueous linear polarization resistance (LPR). The steel electrodes (C1018) were placed in a bath of brine which was deaerated with carbon dioxide. The corrosion rate of the electrode was compared in the absence or presence of the oxyalkylated surfactant.

The brine contained about 3 wt % of sodium chloride. The brine (80 vol %) along with LVT-200 hydrocarbon (20 vol %) was placed into bubble cells and purged with $CO_2$. The brine was continually purged with $CO_2$ to saturate the brine prior to starting the test. The test cells were blanketed with $CO_2$ throughout the duration of the test to maintain saturation. The bubble cells were stirred at 100 revolutions per minute (rpm) for the duration of the test to maintain thermal equilibrium at 80° C.

After 2-3 hours of pre-corrosion time (viz., with no corrosion inhibitor or oxyalkylated surfactant chemistry) 20 ppm of a 10% active poly amine-polyester chemistry with 1% 2-mercaptoethanol in solvent blend was added based on the water phase. This equates to 2 ppm of the active chemistry with 0.2 ppm 2-mercaptoethanol being introduced into the test cell.

Comparison with known quaternary chemistry and imidazoline chemistry at the same activity along with the same amount of 2-mercaptoethanol was made at the same dose rate. A lower concentration was used to differentiate between the chemistries at the same active dose. The percent inhibition was determined by comparing the inhibited corrosion rate at about 14 hours after chemical injection was made to the corrosion rate of the blank after the same exposure time.

Table 3 shows a corrosion rate at about fourteen hours after the corrosion inhibitor was injected into the test.

TABLE 3

| Candidate Chemistry | 2-Mercapto ethanol Activity (%) | Candidate Chemistry Activity (%) | Dosage (ppm) | Corrosion Rate After 14 h of CI Injection (mpy) | % Protection |
|---|---|---|---|---|---|
| Blank | N/A | N/A | 0 | 502 | N/A |
| dimethyl benzyl ammonium chloride | 1 | 10 | 20 | 353 | 30 |
| TOFA:DETA imidazoline salted with acetic acid | 1 | 10 | 20 | 424 | 16 |
| CI-1 | 1 | 10 | 20 | 194 | 61 |
| CI-2 | 1 | 10 | 20 | 187 | 63 |
| CI-3 | 1 | 10 | 20 | 273 | 46 |
| CI-4 | 1 | 10 | 20 | 241 | 52 |
| CI-5 | 1 | 10 | 20 | 197 | 61 |
| CI-6 | 1 | 10 | 20 | 193 | 62 |
| CI-7 | 1 | 10 | 20 | 178 | 65 |
| CI-8 | 1 | 10 | 20 | 208 | 59 |
| CI-9 | 1 | 10 | 20 | 216 | 57 |
| CI-10 | 1 | 10 | 20 | 244 | 51 |

All of the oxyalkylated surfactant chemistries (CI-1 to CI-10) significantly outperformed that of the comparative samples (dimethyl benzyl ammonium chloride or imidalzoine).

What is claimed is:

1. A method of inhibiting corrosion comprising:

introducing into a fluid source containing corrodents a composition comprising an oxyalkylated surfactant having the general structure as shown in Formula I:

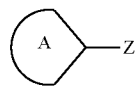
   (Formula I)

wherein A is a phenyl or naphthyl ring, optionally substituted thereof; and Z has the following structure:

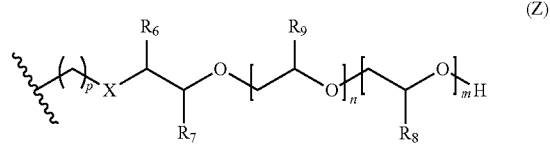
   (Z)

wherein X is —O—; p is 0 or an integer in the range of 1 to 10; R6 is hydrogen, alkyl, or aryl; R7 is an alkyl group having eight to thirty carbon atoms or —(CH$_2$)$_z$—O—R11; R8 and R9 are independently hydrogen, alkyl, or aryl, wherein at least one of R8 and R9 are other than hydrogen, and wherein R8 and R9 are different; R11 is independently hydrogen or alkyl; m is an integer in the range of 2 to 20; n is an integer in the range of 3 to 20; and z is an integer in the range of 1 to 10, and wherein the composition inhibits corrosion.

2. The method of claim 1, wherein introducing comprises injecting or pumping.

3. The method of claim 1, wherein the fluid source is contained in an oil or gas pipeline, a refinery, a distillation column, a stripper tray, or piping.

4. The method of claim 1, wherein the fluid source comprises fresh water, recycled water, salt water, surface water, produced water, a liquid hydrocarbon, or a mixture thereof.

5. The method of claim 1, wherein the fluid source comprises an amount of total dissolved solids in the range of about 0.1% to about 25% weight/weight.

6. The method of claim 1, wherein A is a phenyl ring, optionally substituted thereof.

7. The method of claim 1, wherein the oxyalkylated surfactant has a structure of Formula II:

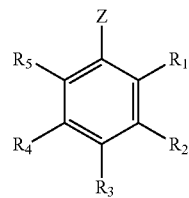

wherein R1, R2, R3, R4, and R5 are independently hydrogen, Z, unsubstituted alkyl, alkoxyl, or two adjacent R groups combine to form a fused naphthyl ring.

8. The method of claim 1, wherein the oxyalkylated surfactant has a structure corresponding to Formula III:

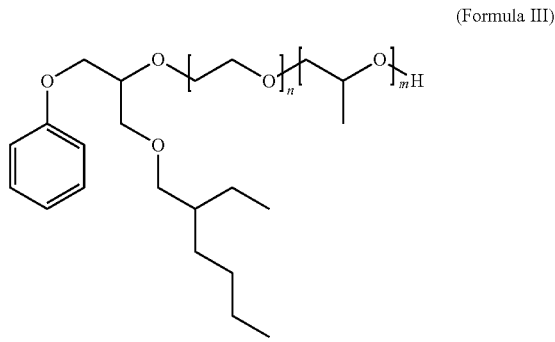
(Formula III)

wherein n is an integer in the range of 10 to 20 and m is an integer in the range of 2 to 12.

9. The method of claim 1, wherein the oxyalkylated surfactant is added to the fluid source in an amount in the range of 1 ppm to 3,000 ppm.

10. The method of claim 1, wherein the composition further comprises an asphaltene inhibitor, a paraffin inhibitor, a scale inhibitor, a demulsifier, a water clarifier, a dispersant, an emulsion breaker, an antifoam, a salt, or a mixture thereof.

11. The method of claim 1, wherein the oxyalkylated surfactant provides at least 50% corrosion protection in a 1018 carbon steel coupon test.

12. The method of claim 1, wherein R9 is —H and R8 is alkyl or aryl.

13. The method of claim 1, wherein R9 is —H and R8 is methyl, ethyl, n-propyl, i-propyl, n-butyl, i-butyl, s-butyl, t-butyl, n-pentyl, i-pentyl, s-pentyl, t-pentyl, or benzyl.

14. The method of claim 1, n is greater than m.

15. The method of claim 14, wherein n is an integer in the range of 10 to 20 and m is an integer in the range of 2 to 12.

16. The method of claim 15, wherein n is an integer in the range of 16 to 18 and m is an integer in the range of 4 to 8.

17. The method of claim 1, wherein R7 is —(CH2)z—O—R11.

18. A method of inhibiting corrosion comprising:
introducing into a fluid source containing corrodents a composition comprising an oxyalkylated surfactant having the general structure as shown in Formula I:

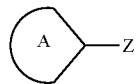

(Formula I)

wherein A is a phenyl or naphthyl ring, optionally substituted thereof; and Z has the following structure:

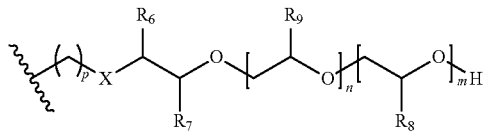

(Z)

wherein X is —O—; p is 0 or an integer in the range of 1 to 10; R6 is hydrogen, alkyl, or aryl; R7 is an alkyl group having eight to thirty carbon atoms or —(CH2)z-O—R11," wherein R11 is independently hydrogen or C4-C22 alkyl; R8 and R9 are independently hydrogen, alkyl, or aryl, wherein at least one of R8 and R9 are other than hydrogen; m is an integer in the range of 2 to 20; n is an integer in the range of 3 to 20; and z is an integer in the range of 1 to 10; and wherein the composition inhibits corrosion.

* * * * *